(12) United States Patent
Bauer

(10) Patent No.: US 8,412,323 B2
(45) Date of Patent: Apr. 2, 2013

(54) REST PHASE HEART PACING

(75) Inventor: Peter T. Bauer, West Linn, OR (US)

(73) Assignee: Inovise Medical, Inc., Beaverton, OR (US)

( * ) Notice: Subject to any disclaimer, the term of this patent is extended or adjusted under 35 U.S.C. 154(b) by 619 days.

(21) Appl. No.: 12/321,647

(22) Filed: Jan. 23, 2009

(65) Prior Publication Data

US 2009/0204165 A1    Aug. 13, 2009

Related U.S. Application Data

(60) Provisional application No. 61/062,702, filed on Jan. 29, 2008.

(51) Int. Cl.
*A61N 1/00* (2006.01)
*A61B 5/04* (2006.01)
*A61B 5/02* (2006.01)

(52) U.S. Cl. .............. 607/9; 607/17; 600/509; 600/514; 600/528

(58) Field of Classification Search ................ 607/9, 17; 600/509, 514, 528
See application file for complete search history.

(56) References Cited

U.S. PATENT DOCUMENTS

| | | | |
|---|---|---|---|
| 5,392,780 A | 2/1995 | Ogino et al. | |
| 5,758,654 A | 6/1998 | Burton-Krahn et al. | |
| 7,039,538 B2 | 5/2006 | Baker, Jr. | |
| 7,074,195 B2 | 7/2006 | Nelson et al. | |
| 7,096,060 B2 | 8/2006 | Arand et al. | |
| 7,113,820 B2 | 9/2006 | Schlegel et al. | |
| 7,171,269 B1 | 1/2007 | Addison et al. | |
| 7,174,203 B2 | 2/2007 | Arand et al. | |
| 7,225,021 B1 | 5/2007 | Park et al. | |
| 7,302,290 B2 | 11/2007 | Bauer | |
| 7,424,321 B2 | 9/2008 | Wariar et al. | |
| 7,431,699 B2 | 10/2008 | Siejko et al. | |
| 7,435,221 B1 | 10/2008 | Bharmi et al. | |
| 7,559,903 B2 | 7/2009 | Moussavi et al. | |
| 7,819,814 B2 | 10/2010 | Gavriely et al. | |
| 8,105,241 B2 | 1/2012 | Nelson et al. | |
| 8,137,283 B2 | 3/2012 | Syeda-Mahmood et al. | |
| 2002/0188329 A1* | 12/2002 | Struble ........................... 607/23 | |

(Continued)

FOREIGN PATENT DOCUMENTS

CA    1256507    6/1989

OTHER PUBLICATIONS

International Search Report, Serial No. PCT/US10/055696, dated Dec. 23, 2010, 13 pages total.

(Continued)

*Primary Examiner* — Nicole F Lavert
(74) *Attorney, Agent, or Firm* — Jon M. Dickinson, Esq.; Robert D. Vantz, Esq.

(57) ABSTRACT

A computer method, employable during an at-rest period of a pacemaker patient, for controlling the operation of the pacemaker so as maximally to support the patient's hemodynamic behavior in a context involving inhibiting fluid overload. The method involves (a) collecting simultaneously occurring ECG and heart-sound information, (b) processing the collected information to obtain at least S3 data, and in certain instances also EMAT and/or % LVST data, (c) utilizing such obtained data, and during the at-rest period, applying (a) pacing rate, (b) pacing intensity, (c) atrio-ventricular delay, and (d) inter-ventricular delay control to the pacemaker. Processing involves (a) calculating from the obtained data an actual, real-time, acoustic cardiographic therapy (AC) value which is to be employed in relation to controlling pacemaker activity, and (b) comparing the actual AC value to a pre-established, related, rest-period-associated, reference AC value to detect differences therebetween, with the utilizing and applying steps being implemented so as to minimize such differences.

2 Claims, 1 Drawing Sheet

U.S. PATENT DOCUMENTS

| | | |
|---|---|---|
| 2003/0187337 A1 | 10/2003 | Tarassenko et al. |
| 2004/0127792 A1* | 7/2004 | Siejko et al. .................. 600/439 |
| 2004/0230105 A1 | 11/2004 | Geva et al. |
| 2005/0027323 A1 | 2/2005 | Mulligan et al. |
| 2005/0080348 A1 | 4/2005 | Stahmann et al. |
| 2005/0222515 A1 | 10/2005 | Polyshchuk et al. |
| 2006/0155202 A1 | 7/2006 | Arand et al. |
| 2007/0038137 A1 | 2/2007 | Arand et al. |
| 2007/0055151 A1 | 3/2007 | Shertukde et al. |
| 2007/0191725 A1 | 8/2007 | Nelson |
| 2008/0021510 A1 | 1/2008 | Mi et al. |
| 2008/0177191 A1 | 7/2008 | Patangay et al. |
| 2008/0255465 A1 | 10/2008 | Nelson |
| 2009/0112107 A1 | 4/2009 | Nelson et al. |
| 2009/0112108 A1 | 4/2009 | Nelson et al. |
| 2009/0165559 A1 | 7/2009 | Lec |
| 2010/0094148 A1 | 4/2010 | Bauer et al. |

OTHER PUBLICATIONS

USPTO Office Action, U.S. Appl. No. 12/315,165, dated Nov. 12, 2010, 9 pages total.

USPTO Office Action, U.S. Appl. No. 11/264,328, dated May 9, 2008, 7 pages total.

USPTO Office Action, U.S. Appl. No. 11/264,328, dated Oct. 16, 2008, 8 pages total.

USPTO Office Action for U.S. Appl. No. 12/321,646 dated Jun. 17, 2011. 9pp.

USPTO Office Action for U.S. Appl. No. 12/288,712 dated Apr. 11, 2011. 5pp.

USPTO Office Action for U.S. Appl. No. 12/321,650 dated Sep. 7, 2011. 8pp.

* cited by examiner

REST PHASE HEART PACING

CROSS-REFERENCE TO RELATED APPLICATIONS

This patent application is related to and claims priority from U.S. Provisional Patent Application Ser. No. 61/062,702, filed Jan. 29, 2008, for Stage-Monitored Physiologic-Demand Heart Pacing, and also relates to subject matter which can be found in U.S. patent application Ser. No. 11/264,328, filed Nov. 1, 2005 for Hemodynamic Assessment/Adjustment, published as U.S. Patent Application Publication No. 2006/0155202, now abandoned, U.S. patent application Ser. No. 11/442,467, filed May 25, 2006, for Cardio-Function Cafeteria System and Methodology, published as U.S. Patent Application Publication No. 2007/0038137, now abandoned, and in U.S. Pat. No. 7,174,203 B1, granted Feb. 6, 2007, for Method and System Relating to Monitoring and Characterizing Heart Condition. These application and patent documents are fully are incorporated herein by reference.

BACKGROUND AND SUMMARY OF THE INVENTION

The present invention is associated generally with the field of acoustic cardiography, and more specifically relates to controlling heartbeat-assisted, pacemaker (implanted or external) pacing in relation to a pacemaker-equipped subject's level of heart-rate activity. Those skilled in the art will recognize that this field of acoustic cardiography involves the cooperative, information-integration use of both heart sounds and ECG information processed in different ways to obtain, selectively, various important heart-functionality parameters which correlate to, and help one to understand, the hemodynamic (pumping and filling) behavior(s) of a subject's heart. Such integration characterizes and underpins important aspects of the present invention.

While it will be very evident to those skilled in the art that the methodology of the present invention may be employed successfully in a number of different heart-pacing manners of operation, a preferred and best-mode approach toward practicing the invention is disclosed herein, for illustration purposes, specifically in the context of biventricular, pacemaker pacing.

State of the art thinking with respect, generally, to the employment and control of pacemaker therapy for a subject who is equipped either with an implanted or an external pacemaker, effectively involves adjusting aspects of the subject's pacing rate in accordance with heart-functionality physiologic demand. Various approaches have been proposed to accomplish this goal. In this context, it is important that any such therapy be applied in a manner which is capable of supporting best-possible heart-functionality behavior in relation to subject activity level and metabolic demand during the different periods in a day.

For example, at nighttime, when the human body reduces its metabolic demand, the intrinsic heart rate of a subject is typically lower in accordance with operation of the subject's neurohumoral control mechanism. This reduced-cycle-rate, nighttime condition is referred to in the medical arts as involving reduced sympathetic tone. During such a time of low (i.e., lower than "normal") subject activity, a time which we refer to herein generally as being a rest-phase time, heart-failure patients, especially at very low activity times, can experience a high fluid load in the heart—a load which the heart muscle normally cannot handle adequately, particularly in a circumstance where the subject is lying down. As a consequence, such patients can go into a decompensated state which leads to fluid being pushed back into the lungs, accompanied by symptoms of shortness of breath which need to be treated just as soon as possible.

In this context, it is typically and conventionally assumed, in accordance with prior-art practice, that a predetermined reduction in a pacemaker's pacing rate will be adequate to deal with such a potential decompensation condition. And, with respect to most of today's currently available pacemakers, medical personnel can preprogram different predetermined pacing rates to apply at different activity-level periods during the day, with heart activity level being generally detectable by means of various conventional mechanical and/or physiologic sensors that are either disposed within, or otherwise operatively associated with, a subject's pacemaker.

The present invention recognizes, generally, that an approach involving increasing a subject's heart-pacing rate during a low (lower than normal)-activity-level rest phase, and especially when the subject is lying down at any time, can potentially prevent the mentioned decompensation. The invention also recognizes, specially and uniquely, that pacing rates employable to deal with decompensation should not be rigidly preprogrammed, as is the case with prior-art, decompensation-minimizing approaches.

Accordingly, key features of the present invention specifically address this just generally outlined rest-phase condition as it relates to the subject's heart functionality, particularly with a focus toward minimizing the mentioned fluid buildup problem, and doing so in a manner which is based upon carefully monitoring (a) a subject's level of heart-rate activity, and (b) one or several identified heart-functionality parameters, and then relatedly adjusting and controlling a pacemaker's (a) pacing rate, (b) pacing intensity, (c) atrio-ventricular (AV) delay and/or (d) inter-ventricular (IV) delay, behavior(s). It should be understood that the "rest-phase" concept expressed herein is treated in the practice of the present invention as a concept which preferably relatively broadly encompasses a wide range of lower-than-"normal" (or high) heart rate levels.

More specifically, and as will be seen, implementation of the present invention focuses, in the related context of feedback-adjusted, rest-phase (not necessarily at night, or while lying down), heart-therapy pacing, on the development and defining (computer calculation) of what is referred to herein as an acoustic cardiographic therapy, or control, (AC) value (also referred to simply as an AC Value). This AC Value "entity", utilizing computer processing, is determined from (i.e., is based upon) one or more heart-functionality parameter(s) that are especially relevant to the heart pumping and filling functions particularly as they are associated with a subject's activity level. It is computed on the basis of key, input, physiologic information, such as heart-sound and ECG information. In this setting, the invention specifically recognizes the special utility, in different circumstances, of several, important heart-functionality parameters as bases for calculating, and then employing, AC Values that are deemed to be the most useful for controlling the rest-phase pacing operation of a pacemaker. These parameters are three in number. They include S3, EMAT and % LVST.

In certain circumstances, the S3 parameter may be used as an averaged singularity for AC-Value calculation purposes. In certain other circumstances, an appropriate averaged and computed mathematical combination of two or all the three parameters may be the best to use. Non-exclusive illustrations of averaging and mathematical combining of heart-functionality parameter values involved in the calculation of AC values are given below.

DEFINITIONS

At this point, it will be useful to define certain terms and terminology which appear(s) in the text herein.

S1—The peak-to-peak measurement of the amplitude of the first heart sound (based predominantly on mitral valve closure).

S2—The peak-to-peak measurement of the amplitude of the second heart sound (based predominantly on aortic valve closure).

S3—The strength of the third heart sound based on the intensity and persistence of that sound. Conventionally, acoustic cardiography provides a value for S3 strength in the range of 1 to 10. If this value equals or exceeds 5.0, a conventional algorithm employed herein declares that a third heart sound is present. With relatively normal heart rates, the third heart sound occurs typically about 0.12- to about 0.16- seconds after the second heart sound. The most likely explanation for the production of the third heart sound is that vigorous and excessively rapid filling of blood into a stiff ventricle is suddenly halted, causing audible vibrations. In persons generally older than about 40-years, the third heart sound has been shown to indicate elevated filling pressure and systolic dysfunction. This S3 sound is associated with an abnormal diastolic filling pattern, and almost all persons with pseudonormal, or restrictive, filling patterns exhibit third heart sounds.

% LVST—Left ventricular systolic time measured as the time from the mitral component of the first heart sound to the aortic component of the second heart sound. % LVST is computed as LVST divided by the dominant RR interval (the time between two consecutive R waves in an ECG signal). % LVST indicates how much of the cardiac cycle is occupied by systole (pump function) versus diastole (filling). A normal % LVST value lies usually in the range of about 35% to about 45%.

EMAT—The electromechanical activation time measured from Q-wave onset (from ECG information) to the time of closure of the mitral valve within the first heart sound. The time value of EMAT reflects the time required for the left ventricle to generate sufficient force to close the mitral valve, and is therefore related to the acceleration of the pressure curve in the left ventricle.

AC Value—While other approaches may be made if desired, an AC Value herein, generally, is a computer-calculated, numeric value based upon simple, common-parameter averaging, and arithmetic combining (adding, subtracting, multiplying, etc. of the respective, common-parameter averages associated with plural, different parameters), of the determined values of user-selected parameters (one or more) drawn from the list of the three, heart-functionality parameters mentioned above, acquired over a user-selected, cardiac-cycle-collection time period, such as a ten-second time period.

As an illustration, if two heart-functionality parameters (as distinguished from a singular, selected-parameter situation), A and B, have been selected to form the basis for a calculated AC Value, the respective A and B values obtained from the plural heart cycles acquired during a given cardiac-cycle-collection time period are individually averaged to produce an average A value and an average B value. These two, average, parameter-specific values are then mathematically combined as desired, for example by addition, subtraction, multiplication, etc., to produce a resulting, usable AC Value. If desired, in such a plural-parameter use situation, weighted mathematical combining may be employed to recognize differential importances relating to the selected heart-functionality parameters.

Actual AC Value—an AC Value which is calculated, in real-time, based upon a selected number of cardiac cycles acquired from a subject during implementation and operation of the methodology of the invention.

Reference AC Value—an AC Value based upon one or more of the three, mentioned, selected heart-functionality parameters, determined from data acquired from a subject at one or more point(s) in time when that subject's heart appears to be operating in a normal and satisfactory rest-phase manner. In the practice of the invention, there may be several reference AV Values which relate to several, different, user-desired and identified rest-phase and more active conditions. Such an AC Value, or Values, may also be drawn from an available database of heart-functionality data derived from a selected population of people having characteristics which are deemed to be similar to those possessed by a particular subject. A reference AC Value may also be calculated readily by a suitably algorithmically programmed digital computer which is provided, as by independent user input, with a user-selected, assumed heart rate regarding and from which the user intends to dictate the establishment of a relevant reference AC Value. This approach is discussed below herein in the context of an open-loop practice of the invention.

In general terms, the present invention involves a computer-performed method, employable during an at-rest period of a pacemaker patient (subject) having heart failure and being at risk for fluid overload, for adjusting and controlling the operation of the subject's pacemaker so as to effect pacing in a manner maximally supporting the subject's hemodynamic behavior in a context involving inhibiting fluid overload. This method features the steps of (a) collecting from a subject, effectively in a continuum during such a rest-phase period, simultaneously occurring ECG and heart-sound continuum information, (b) computer-processing the collected continuum information to obtain at least S3 data, and (c) effectively utilizing such at least S3 data, and during the mentioned at-rest period, appropriately applying at least one of (a) pacing rate, and (b) arterial-ventricular delay, controls to the pacemaker.

In a more specific sense, this method is one wherein the mentioned computer-processing involves (a) calculating, based on the S3 data obtained from the collected continuum data, an actual, real-time, acoustic cardiographic therapy (AC) value which is to be employed in relation to pacemaker adjusting and controlling, and (b) comparing such a calculated, actual AC value to a pre-established, related, rest-period-associated, reference AC value to detect differences therebetween, with the utilizing and applying steps being conducted so as to minimize such differences.

Another manner of expressing the methodology of the invention involves computer-processing the collected continuum information so as to obtain, in addition to S3 data, at least one of EMAT and % LVST data, and effectively utilizing such computer-processed and obtained, "augmented" data for applying at least one of (a) pacing rate, (b) pacing intensity, (c) atrio-ventricular (AV) delay and (d) inter-ventricular (IV) delay, controls to the pacemaker.

A more thorough understanding of the invention will be obtained by reference to the following detailed description of the preferred and best-mode embodiment of the invention in connection with the accompanying drawings.

DESCRIPTIONS OF THE DRAWINGS

DETAILED DESCRIPTION OF THE INVENTION

Figure 1:
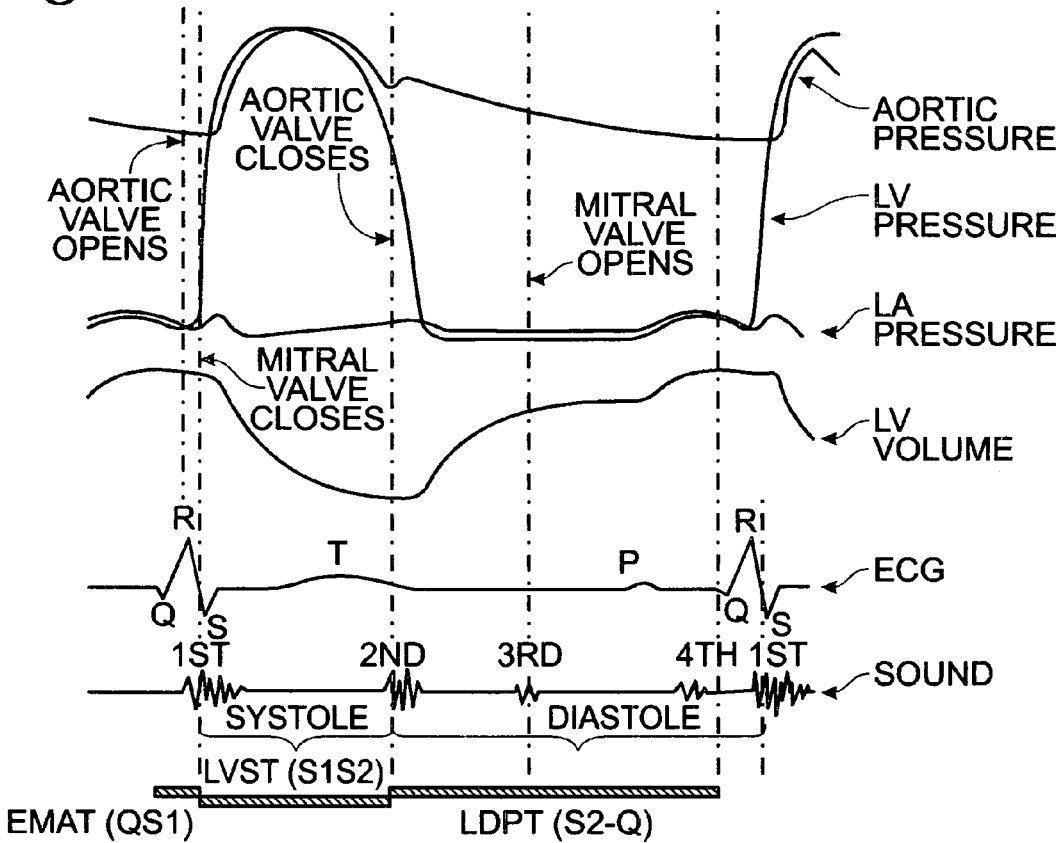
FIG. 1 is a graphical, time-based presentation of ECG data, heart sounds, certain heart functions, and aspects of several parameters which are relevant to practice of the present invention.

Turning now to the drawings, and beginning with FIG. 1, for those who are generally skilled in the relevant art, the content of the time-based graphical display which is presented in this figure is completely familiar, and requires no particular elaboration. As will be observed, this content plainly illustrates the characteristics of the several, particular, different heart-functionality (physiologic) parameters, both electrical and acoustical, which differentially play roles in the AC-Value defining (calculating) practice of the present invention. These parameters, whose respective definitional characteristics which are relevant herein have been set forth above, include S1, S2, S3, % LVST and EMAT.

Figure 2:
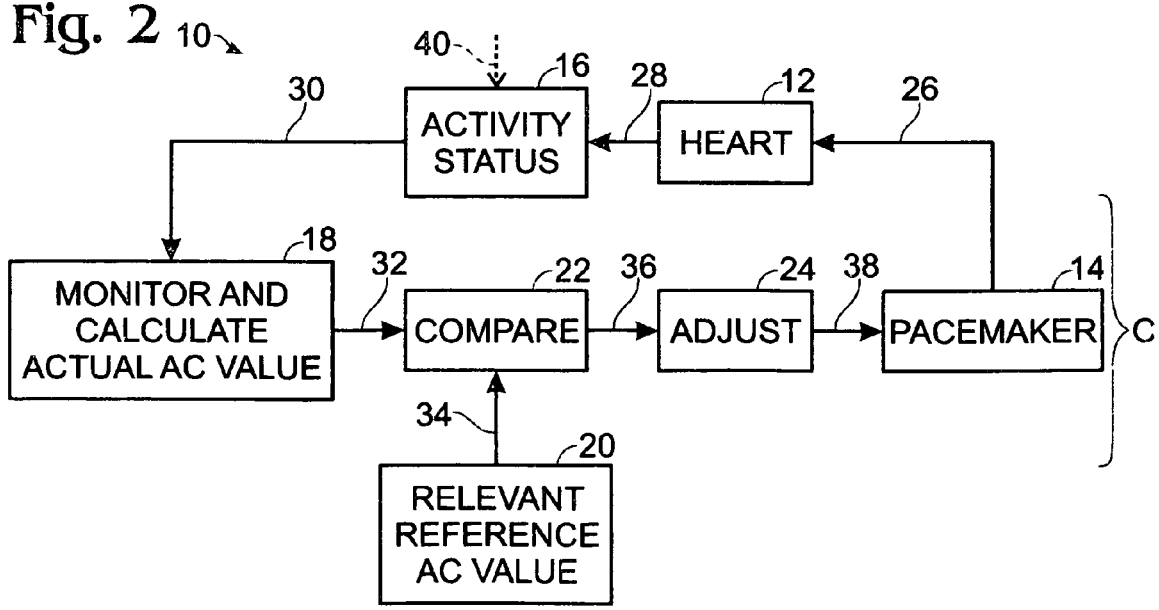
FIG. 2 is a block/schematic diagram illustrating the overall methodology of the present rest-phase pacemaker control invention.

Switching attention to FIG. 2, indicated generally at 10 is a block/schematic diagram which illustrates the overall architectural layout, and the key features, of the methodology of the present invention. Methodology 10 is specifically illustrated and described herein in the context of a person—a subject—(not specifically illustrated in the drawings) who has a heart-failure (poor pumping and filling) condition, and who has been equipped with a heart-pacing device in the form of a biventricular pacemaker. Such a device may be either an implanted (internal) device, or an external device, with respect to which the features of the present invention are equally applicable. However, for invention description purposes herein, an assumption is made that such a device is of the implanted, internal category.

Continuing with a discussion regarding FIG. 2, shown more specifically at 10, in solid lines, are a preferred, and best-mode, embodiment of, and manner of practicing, the methodology of the present invention. As shown in solid lines in FIG. 2, methodology 10 is illustrated in the form of a closed feedback control loop which includes seven blocks 12, 14, 16, 18, 20, 22, 24. These blocks are operatively interconnected by information and/or control communication connections represented by arrow-headed lines 26, 28, 30, 32, 34, 36, 38.

Block 12 represents the mentioned, non-illustrated-subject's heart, and block 14 represents a heart-pacing therapy device in the form, as just suggested above, of a biventricular pacemaker. Pacing pulses are delivered from pacemaker 14 to heart 12 via communication connection 26.

Blocks 16-24, inclusive, represent both structure and methodology which is implemented in an appropriately, and conventionally, algorithmically programmed digital computer represented by a bracket C which appears adjacent the right side of FIG. 2. Thus, these five blocks may be understood in FIG. 2 to represent directly such a computer.

Algorithmic programming in computer C, which programming includes, as will be seen, an architecture that is suitable for implementing all of the still-to-be-described (a) monitoring, (b) value-calculating, (c) comparing, and (d) pacemaker control tasks, as well as any other computational tasks that may be desired, may be structured in various different, entirely conventional ways that are all well within the skills and knowledge possessed by those generally skilled in such programming arts. This condition of readily understandable programming suited to the practice of the present invention is especially made clear in the contexts of the teachings of the drawings presented herein, and of the operational description of the invention set forth below. Accordingly, programming details, and details of related algorithmic architecture associated with, and installed in, computer C, which details form no part of the present invention, are not elaborated herein.

Received in block 18, as delivered via communication connection 28, block 16 (more to be said about this block later herein), and communication connection 30, are ECG and heart-sound categories of information (heart-functionality information) that are acquired in conventional fashions from heart 12. One should note here that the present invention is not concerned with any specific manner or manners in which such heart-functionality information is acquired, and, accordingly, no specific details of such acquisition are set forth herein. Suffice it to say that each "event" of gathering such information takes place over a user-selectable, pre-determined, and pre-computer-programmed interval of time, such as the previously mentioned ten-second cardiac-cycle-collection time, which is sufficient to permit the capture of heart data from a plurality of real-time, i.e., current, cardiac cycles. For the purpose of illustration herein, an assumption is made, for invention-disclosure purposes, that, under the control of computer C, ten such cycles are obtained in each of the mentioned, ten-second, cardiac-cycle-collection time periods. The rate of cardiac-cycle-collection of heart data is a matter of user choice, programmed in to computer C.

Block 18, which is labeled "Monitor and Calculate Actual AC Value", recurrently receives (monitors) and processes successive, cardiac-cycle-collection collections" of this ECG and heart-sound information to calculate and identify therein per-cardiac-cycle values for whichever one or ones of the three, above-identified, heart-functionality parameters has (have) been chosen by a user to be employed in the practice of this invention for effecting pacing control over the operation of pacemaker 14. For the purpose of ongoing description of the invention methodology herein, and just for single-illustration purposes, we will further assume, at least initially, that the parameter S3 has been chosen as a singularity to form the basis for pacemaker-operation control. Thus, and in accordance with the invention, and within block 18, a computer calculation is therein performed, for each cardiac-cycle-collection cycle of heart data, to generate an actual AC Value through a process of simple averaging of the several collected and calculated S3 values drawn from each cardiac cycle. This calculated, actual AC Value is supplied to block 22 (labeled "Compare") via communication connection 32.

Additionally, throughout the solid-line, closed, feedback-loop operation of the methodology pictured in FIG. 2 at 10, computer C recurrently reviews ECG and heart-sound information received by block 18 in order to assess current, real-time heart-activity (cycle-rate) level. This assessment is performed in block 16 ("Activity Status") by looking specifically at one or more of the S3, EMAT, and % LVST parameters contained in the received continuum data. From this activity-level-monitoring behavior, the computer determines, also on a real-time basis, which of perhaps several, different, potentially relevant, reference AC Values that are memory stored effectively in block 20, to employ with respect to certain comparison activity which will shortly be explained that takes place in the realm of block 22. With regard to the memory presence in computer C, preferably, of several (normally at least two), different, relevant, reference AC Values, the granularity of (differentiation between) these values is completely pre-chosen by the user and suitably programmed into the memory of the computer. These reference AC Values will be chosen to reflect predetermined "norms" that are to be considered in the practice of the invention as being "to-be-achieved control targets" for real-time-observed, actual AC Values that are recurrently calculated in relation to actual subject heart-rate activity level throughout a day. The notation just immediately above that there will be preferably at least two such reference values is made to confirm that the methodology of the invention will be able to "handle", at least in a kind of "gross" manner, basically differing periods of (a) high, and (b) low (rest phase), activity levels.

In block 22, a comparison takes place between each just-mentioned, continuum-data supplied, calculated, real-time actual AC Value and a computer-chosen, reference AC Value—the latter being furnished to block 22 via communication connection 34 from block 20, wherein an appropriate location in the memory of computer C has previously stored such a reference value. The reference AC Value selected by computer C each time for use is based preferably upon the then level of heart-rate activity as determined in block 16 by the computer from the most current received and monitored, heart-functionality, continuum data.

The general definition of reference AC Value has, of course, been provided earlier herein. For the purpose of ongoing description of the methodology of the invention, we will assume that this reference value has been based upon previously acquired, real-time heart-functionality data derived directly from the subject, per se, during a prior span of time when medical personnel have determined that the subject's heart is performing in normal and satisfactory pumping and filling manners in relation to a heart-rate activity level which is most closely like the currently detected heart-rate activity level. This reference AC Value, for the currently underway description of the invention, takes the form of a calculated, appropriately simply averaged value drawn from the appropriate pre-collection of S3-based AC Values, and which is "right" for the current, subject-cardiac-cycle, activity-rate condition.

From the comparison which is produced in block 22, any difference which is detected between the actual AC Value, as calculated, and the stored, reference AC Value which is chosen to be used, is noted and supplied to block 24 via communication connection 36. The AC-Value difference information which is passed by way of connection 36 to block 24 causes block 24 to send, by way of communication connection 38, to pacemaker 14 a control signal, or signals, which effect(s) an operational adjustment, or adjustments, as necessary, to re-form the pacing operation of the pacemaker so as to stimulate heart 12, via connection 26, in a manner intended to minimize the difference between a calculated, current, actual AC Value and the just previously chosen-for-comparison, relevant, reference AC Value.

This adjustment, of course, is aimed at furnishing heart therapy from pacemaker 14 which is deemed most appropriate for improving the pumping and filling behaviors of heart 12, and especially for inhibiting, if not completely preventing (an ideal) the serious problem of fluid overload in various categories of rest-phase heart behavior. The preferred adjustments take the form of specific adjustments that are made in one or more of the pacing rate, pacing intensity, AV delay, and IV delay operational behavior(s) of the pacemaker.

Throughout the time of pacemaker operation—day and night—and in accordance with the unique methodology of the present invention, recurrent heart-functionality monitoring, and calculating of actual AC Values, based on specially recognized, featured and selected heart functionality parameters, take place, followed by respective comparison activities in block 22, as explained, thereby to produce effective operational control adjustments as needed which are delivered as control signals by block 24 to the pacemaker in a continual feedback effort to maintain, as closely as possible, an equality of actual and reference AC Values. As was mentioned earlier, the frequency of recurrent monitoring, and of associated, actual AC Value calculations, and actual and reference AC-Value comparisons, is a matter of user choice, and is programmed appropriately into computer C.

Completing now a description of what is shown in FIG. 2, illustrated fragmentarily by an arrow-headed, dashed line 40 in this figure is a modified form of the invention which effectively operates as an open-loop approach to entering an activity-status heart-rate level into the practice of the invention for use in computer-calculating a relevant, reference AC Value placeable in the computer memory location which is represented by block 20 in this figure. Any suitable open-loop approach may be employed to implement this modification of the invention, which modification might, though not necessarily will, replace, at least temporarily, the close-loop operation which has been described previously regarding FIG. 2. For example, a medical person attending to a particular subject under certain circumstances might decide to enter one or several "open-loop", assumed heart rates for subsequent calculation of associated reference AC Value(s) for use under certain circumstances in the practice of the invention.

It is also entirely possible to implement, periodically, and only for certain point in time, a momentary "open-loop" style of behavior in the methodology of the invention which, except at a certain point, or at certain points, in time when employed, will not otherwise operate to interrupt the closed-loop operation which has principally been described above for practice of the invention.

The present invention thus proposes a unique rest-phase, heart-pacing-device control methodology. This methodology may be expressed as a computer-performed method, employable during an at-rest period (broadly defined as set forth above) of a pacemaker patient having heart failure and being at risk for fluid overload, for adjusting and controlling the operation of the patient's pacemaker so as to effect pacing in a manner maximally supporting the patient's hemodynamic behavior in a context involving inhibiting fluid overload. The method generally includes the steps of (a) collecting, effectively in a continuum during such an at-rest period, simultaneously occurring ECG and heart-sound continuum information, (b) computer-processing the collected continuum information to obtain at least S3 data, and (c) effectively utilizing such at least S3 data, and during the mentioned at-rest period, appropriately applying at least one of (a) pacing rate, (b) pacing intensity, (c) atrio-ventricular delay, and (d) inter-ventricular delay control to the pacemaker.

The method further may be described as one wherein the mentioned computer-processing involves (a) calculating, based on the S3 data obtained from the collected continuum data, an actual, real-time, acoustic cardiographic therapy (AC) value which is to be employed in relation to the adjusting and controlling steps, and (b) comparing such calculated, actual AC value to a pre-established, related, rest-period-associated, reference AC value to detect differences therebetween, and the mentioned utilizing and applying steps are conducted so as to minimize such differences.

In still other language, the invention may be viewed as a computer-performed method somewhat like that just expressed above including, as steps, (a) collecting, effectively in a continuum, during an at-rest period, simultaneously occurring ECG and heart-sound continuum information, (b) computer-processing the collected continuum information to obtain S3 data and at least one of EMAT and % LVST data, and (c) effectively utilizing such computer-processed data, and during the mentioned at-rest period, appropriately applying at least one of (a) pacing rate, (b) pacing intensity, (c) atrio-ventricular delay, and (d) inter-ventricular delay control to the pacemaker.

Preferably, although not necessarily, all structure, firmware and software which are relevant to the practice of the invention, including a programmable digital computer with an appropriate memory, and all operational algorithmic software, are effectively "onboard" and installed as "component parts/aspects" of the pacemaker which is employed.

Accordingly, while a preferred and best-mode embodiment of, and manner of practicing, the invention have been illustrated and described herein, and a single modification suggested, it is appreciated that further variations and modifications thereof may be made within the scope of the invention and without departing from its spirit.

I claim:

1. An at-rest-dedicated, acoustic-cardiography method, utilizing the technique of at-rest, real-time, computer-monitored-and-performed difference minimizing between actual real-time, and available-reference, AC (acoustic cardiographic) values that are based upon at-rest-patient-relevant, acquired and computer-processed heart-sound and/or ECG data involving a pacemaker patient having heart failure and being at risk for fluid overload, for adjusting and controlling the patient's pacemaker's operational (a) pacing rate, (b) pacing intensity, (c) atrio-ventricular delay, and (d) inter-ventricular delay so as to effect pacing in a manner maximally supporting the patient's hemodynamic behavior in a context involving inhibiting real-time at-rest fluid overload, said method comprising

- collecting in a continuum, solely during an at-rest period of the subject pacemaker patient, simultaneously occurring ECG and heart-sound continuum information,
- obtaining, for computer processing, from the collected continuum information at least S3 heart-sound data,
- utilizing the obtained data, and employing at least data averaging, calculating an actual, real-time, acoustic cardiographic (AC) value,
- comparing in real time the calculated, actual, real-time AC value to a pre-established, related, at-rest-period-associated, available reference AC value to detect differences therebetween,
- during the mentioned at-rest period, and in the associated real time, appropriately applying, to the operation of the pacemaker, adjustment-based change control over at least one of the pacemaker's operational (a) pacing rate, (b) pacing intensity, (c) atrio-ventricular delay, and (d) inter-ventricular delay so as to minimize the detected AC-value differences, and
- by said applying, effecting pacing by the pacemaker in a manner maximally supporting the patient's hemodynamic behavior through inhibiting fluid overload.

2. The method of claim 1, wherein said obtaining of data further includes obtaining at least one of EMAT and % LVST data.

* * * * *